či et al.

United States Patent
Bassin et al.

(10) Patent No.: US 9,782,121 B2
(45) Date of Patent: Oct. 10, 2017

(54) DISTINGUISHING CLOSED AND OPEN RESPIRATORY AIRWAY APNEAS BY COMPLEX ADMITTANCE VALUES

(71) Applicant: ResMed Limited, Bella Vista (AU)

(72) Inventors: David John Bassin, Sydney (AU); John David Oates, Castle Hill (AU); Ronald James Huby, North Epping (AU); Benriah Goeldi, Freiburg (DE)

(73) Assignee: ResMed Limited (AU)

( * ) Notice: Subject to any disclaimer, the term of this patent is extended or adjusted under 35 U.S.C. 154(b) by 0 days.

(21) Appl. No.: 15/420,282

(22) Filed: Jan. 31, 2017

(65) Prior Publication Data

US 2017/0135630 A1 May 18, 2017

Related U.S. Application Data

(60) Continuation of application No. 14/643,233, filed on Mar. 10, 2015, now Pat. No. 9,597,012, which is a
(Continued)

(51) Int. Cl.
*A61B 5/08* (2006.01)
*A61B 5/00* (2006.01)
(Continued)

(52) U.S. Cl.
CPC ........ *A61B 5/4818* (2013.01); *A61B 5/085* (2013.01); *A61B 5/087* (2013.01);
(Continued)

(58) Field of Classification Search
CPC ........ A61B 5/085; A61B 5/087; A61B 5/4818
See application file for complete search history.

(56) References Cited

U.S. PATENT DOCUMENTS

| 4,022,193 A | 5/1977 | Franetzki et al. |
| 4,197,859 A | 4/1980 | Prestele |

(Continued)

FOREIGN PATENT DOCUMENTS

| CN | 1035245 A | 9/1989 |
| CN | 1046397 A | 10/1990 |

(Continued)

OTHER PUBLICATIONS

Australian Examination Report for Application No. 2013213685 dated Feb. 6, 2015.
(Continued)

*Primary Examiner* — Christian Jang
(74) *Attorney, Agent, or Firm* — Lerner, David, Littenberg, Krumholz & Mentlik, LLP

(57) ABSTRACT

Methods and apparatus are disclosed for determining the occurrence of a closed or open apnea. Respiratory air flow from a patient is measured to give an air flow signal. The determination of an apnea is performed by applying an oscillatory pressure waveform of known frequency to a patient's airway, calculating a complex quantity representing a patient admittance (12) and comparing its value with ranges (14,16) indicative of open or closed apneas. The method distinguishes open from closed apneas even when the model used to calculate admittance is not based on details of the respiratory apparatus. In addition the patient admittance may be compared with admittance during normal breathing to avoid having to characterize the airway.

19 Claims, 5 Drawing Sheets

Related U.S. Application Data division of application No. 12/376,136, filed as application No. PCT/AU2007/001257 on Aug. 30, 2007, now Pat. No. 9,028,423.

(60) Provisional application No. 60/916,147, filed on May 4, 2007, provisional application No. 60/823,973, filed on Aug. 30, 2006.

(51) Int. Cl.
*A61M 16/00* (2006.01)
*A61B 5/085* (2006.01)
*A61B 5/087* (2006.01)

(52) U.S. Cl.
CPC . *A61M 16/0069* (2014.02); *A61M 2016/0027* (2013.01); *A61M 2016/0033* (2013.01); *A61M 2205/15* (2013.01); *A61M 2205/3303* (2013.01); *A61M 2230/46* (2013.01)

(56) References Cited

U.S. PATENT DOCUMENTS

| | | | |
|---|---|---|---|
| 5,134,995 | A | 8/1992 | Gruenke et al. |
| 5,148,802 | A | 9/1992 | Sanders et al. |
| 5,245,995 | A | 9/1993 | Sullivan et al. |
| 5,549,106 | A | 8/1996 | Gruenke et al. |
| 5,704,345 | A | 1/1998 | Berthon-Jones |
| 5,845,636 | A | 12/1998 | Gruenke et al. |
| 5,881,724 | A | 3/1999 | Graetz et al. |
| 6,015,388 | A | 1/2000 | Sackner et al. |
| 6,142,952 | A | 11/2000 | Behbehani et al. |
| 6,287,264 | B1 | 9/2001 | Hoffman |
| 6,675,797 | B1 | 1/2004 | Berthon-Jones |
| 2004/0123866 | A1 | 7/2004 | Berthon-Jones |
| 2005/0178385 | A1 | 8/2005 | Dellaca'et al. |
| 2005/0284469 | A1 | 12/2005 | Tobia et al. |
| 2007/0093724 | A1 | 4/2007 | Nakano |
| 2010/0024819 | A1 | 2/2010 | Tiedje |

FOREIGN PATENT DOCUMENTS

| | | |
|---|---|---|
| CN | 1726865 A | 2/2006 |
| CN | 1799501 A | 7/2006 |
| EP | 0651971 A1 | 5/1995 |
| EP | 0927538 A2 | 7/1999 |
| EP | 1488743 A2 | 12/2004 |
| GB | 1500627 A | 2/1978 |
| JP | 02271835 | 11/1990 |
| JP | 06503484 A | 4/1994 |
| JP | 2001500416 A | 1/2001 |
| JP | 2001513387 A | 9/2001 |
| JP | 2001522662 A | 11/2001 |
| JP | 2002010498 A | 1/2002 |
| JP | 2002204830 A | 7/2002 |
| JP | 2002291889 A | 10/2002 |
| JP | 2003525647 A | 9/2003 |
| JP | 2004500969 A | 1/2004 |
| JP | 2004522483 A | 7/2004 |
| JP | 2005214049 A | 8/2005 |
| JP | 2006506137 A | 2/2006 |
| JP | 2006506139 A | 2/2006 |
| JP | 2006516100 A | 6/2006 |
| WO | 8201815 A1 | 6/1982 |
| WO | 9211054 A1 | 7/1992 |
| WO | 03103493 A1 | 12/2003 |
| WO | 2005009501 A2 | 2/2005 |
| WO | 2005068005 A1 | 7/2005 |
| WO | 2005104944 A1 | 11/2005 |
| WO | 2006099670 A1 | 9/2006 |

OTHER PUBLICATIONS

Chinese Office Action for Application No. 201210393964.8 dated Mar. 10, 2015.
Extended European Search Report for Application No. 16158562.5 dated Jul. 5, 2016.
International Search Report & Written Opinion for Application No. PCT/AU2007/001257 dated Dec. 7, 2007.
R. Farre et al: "Assessment of bronchial reactivity by forced oscillation admittance avoids the upper airway artefact", European Respiratory Journal, vol. 13, No. 4, Apr. 1, 1999 (Apr. 1, 1999), p. 761-766, XP055112713.

DISTINGUISHING CLOSED AND OPEN RESPIRATORY AIRWAY APNEAS BY COMPLEX ADMITTANCE VALUES

CROSS-REFERENCE TO RELATED APPLICATIONS

This application is a continuation of U.S. application Ser. No. 14/643,233, filed Mar. 10, 2015 which is a divisional of U.S. patent application Ser. No. 12/376,136, filed on Feb. 3, 2009, which application is a national phase entry under 35 U.S.C. §371 of International Application No. PCT/AU2007/001257 filed Aug. 30, 2007, which claims priority from U.S. Provisional Patent Application No. 60/916,147 filed May 4, 2007 and U.S. Provisional Patent Application No. 60/823,973 filed Aug. 30, 2006, all of which are hereby incorporated herein by reference.

FIELD OF THE INVENTION

This invention relates to the discrimination of open and closed apneas (i.e. the complete cessation of breathing). In an open apnea the airway is patent, while in a closed apnea there is a total obstruction of the airway. The discrimination between such apneas is advantageous in the diagnosis and treatment of respiratory conditions that have adverse effects on a person's wellbeing.

BACKGROUND OF THE INVENTION

The expression "airway" as used herein is to be understood as the anatomical portion of the respiratory system between the nares and the bronchi, including the trachea. The expression "respiration" is to be understood as the continually repeating events of inspiration (inhaling) followed by expiration (exhaling).

In the Sleep Apnea syndrome a person stops breathing during sleep. Cessation of airflow for more than 10 seconds is called an "apnea". Apneas lead to decreased blood oxygenation and thus to disruption of sleep. Apneas are traditionally categorized as either central, where there is no respiratory effort, or obstructive, where there is respiratory effort. With some central apneas, the airway is patent, and the subject is merely not attempting to breathe. Conversely, with other central apneas and all obstructive apneas, the airway is not patent (i.e. occluded). The occlusion is usually at the level of the tongue or soft palate. The airway may also be partially obstructed (i.e. narrowed or partially patent). This also leads to decreased ventilation (hypopnea), decreased blood oxygenation and disturbed sleep.

The dangers of obstructed breathing during sleep are well known in relation to the Obstructive Sleep Apnea (OSA) syndrome. Apnea, hypopnea and heavy snoring are recognized as causes of sleep disruption and risk factors in certain types of heart disease. Increased upper airway resistance (Upper Airway Resistance syndrome) during sleep without snoring or sleep apnea also can cause sleep fragmentation and daytime sleepiness.

The common form of treatment of these syndromes is the administering of Continuous Positive Airway Pressure (CPAP). Briefly stated, CPAP treatment acts as a pneumatic splint of the airway by the provision of a positive pressure, usually in the range 4-20 cm $H_2O$. The air is supplied to the airway by a motor driven blower or other flow generator (FG) whose outlet passes via an air delivery hose to a nose (or nose and/or mouth) mask sealingly engaged to a patient's face. An exhaust port is provided in the delivery tube proximate to the mask. More sophisticated forms of CPAP, such as bi-level CPAP and autosetting CPAP, are described in U.S. Pat. Nos. 5,148,802 and 5,245,995 respectively.

As noted, central apneas need not involve an obstruction of the airway, and often occur during very light sleep and also in patients with various cardiac, cerebrovascular and endocrine conditions unrelated to the state of the upper airway. In those cases where the apnea occurs without obstruction of the airway, there is little benefit in treating the condition by techniques such as CPAP. In automated CPAP systems, it is important to accurately distinguish apneas with an open airway from apneas with a closed airway, in order to avoid inappropriately increasing the CPAP splinting air pressure. Such unnecessary increases in pressure reflexly inhibit breathing, further aggravating the breathing disorder.

U.S. Pat. No. 5,245,995 describes how snoring and abnormal breathing patterns can be detected by inspiration and expiration pressure measurements while sleeping, thereby leading to early indication of preobstructive episodes or other forms of breathing disorder. Particularly, patterns of respiratory parameters are monitored, and CPAP pressure is raised on the detection of pre-defined patterns to provide increased airway pressure to, ideally, prevent the occurrence of the obstructive episodes and the other forms of breathing disorder.

Prior Use of the Forced Oscillation Technique

U.S. Pat. No. 5,704,345, entitled "Detection Of Apnea And Obstruction Of The Airway In The Respiratory System" describes various techniques for sensing and detecting abnormal breathing patterns indicative of obstructed breathing, including the determination of airway patency by a forced oscillation technique (FOT) in which an oscillatory pressure waveform of known frequency is applied to a patient's airway and the magnitude of the component of an airflow signal at the known frequency induced by the oscillatory pressure waveform is calculated and compared with a threshold value. The present invention is an improvement of the methods and apparatus disclosed in the '345 patent.

The use of pressure oscillations at frequencies of the order of 4 Hz to determine airway patency was used in the ResMed AutoSet Clinical automatic CPAP device and the PII Plus. In these machines which used FOT, the pressure was measured at the mask, and the flow was measured very close to the mask, on the patient side of the mask vent. The present invention finds an advantage in measuring pressure and flow at or near the flow generatory at least for analyzing the effect of the forced oscillation technique.

The prior art implementations of FOT are less accurate in distinguishing between closed and open apneas when there is present moderate leak and moderate "resistance" in the airpath between the flow generator and the patient. For example, a passive patient simulation consisting of a 3-4 cm $H_2O/(l/s)$ resistance, with an adjustable leak, would indicate an open airway at a leak of 15 l/min and a closed airway at a leak of 20 l/min. What is needed is a system that more accurately distinguishes between open and closed apneas. In particular what is needed is a system that goes beyond treating the components of the airpath simply as nonlinear resistances and which utilizes an algorithm that takes into account the capacitive and inductive components of the airpath impedance.

BRIEF SUMMARY OF THE INVENTION

In a prior filed U.S. Provisional Patent Application Ser. No. 60/823,973, filed Aug. 30, 2006, it was disclosed that an effective method for discriminating between closed and open respiratory airway apneas was by determining the complex admittance of a patient airway and comparing the absolute value of the complex admittance to threshold values. That disclosure employed an algorithm that takes into account the patient circuit and models each component (patient circuit, vent flow and leak) in order to determine the patient pressure and flow. In particular, the small-signal hose pressure drop was modeled as a two port network in which the parameters were a function of mean flow. The present invention includes embodiments that are an improvement on that technique by including more information from that complex quantity, namely the phase angle of the admittance, or both the real and imaginary components of the complex quantity, in discriminating between open and closed apneas. In particular, it has been surprisingly discovered by analyzing data previously identified with open and closed apneas, that there is significantly better separation of the data if the phase angle of the admittance is taken into account. In addition, the previous system is simplified by modeling the pressure drop without having to measure the AC impedance of the patient circuit across a range of flows.

A plot of the magnitude of admittance against the phase of admittance provides distinct areas of the plot that indicate open or closed airways. Alternatively, the real part of the admittance may be plotted against the imaginary part in an Argand diagram, resulting again in distinct areas of the diagram being associated with open and closed apneas.

The invention provides an improved method and apparatus for treating a patient subject to apneas. In particular it relies upon improved methods for determining whether an apnea is closed or open, by identifying sets of values of the complex patient admittance that are respectively characteristic of open or closed apneas. The admittance is the reciprocal of the complex impedance of the apparatus parameterized for example as a two port model of flow impedance or determining resistive and inertial components from a theoretical model employing empirically derived resistive constants and theoretically determined flow inertance constants.

A sinusoidal (e.g. 4 Hz) pressure oscillation is applied at the input to the airpath, while flow and pressure is measured both at the input and output of the airpath. Based upon the two port model or the more theoretical hose drop model, the admittance is determined from the AC component of the patient airflow (found by subtracting the AC components of vent flow and leak) and the AC component of the mask pressure. The vent flow, in turn, is determined from an improved quadratic relationship to mask pressure in the case of the two port model, or a linearized calculation in the more theoretical hose drop model. The leak is determined from an estimated leak coefficient. The calculation of AC components of these quantities is improved over prior estimations by using Fourier sine and cosine components at the input oscillation frequency rather than by approximating an orthonormal set of functions by square waves.

The invention discloses a method for determining patency of the airway of a patient, the method comprising the steps of:
applying an oscillatory pressure waveform of known frequency to the patient's airway;
measuring respiratory air flow and pressure at the flow generator;
calculating the AC values of flow and pressure at the mask from a 2-port impedance model,
determining that the airway is patent by determining whether the complex admittance is in a region characteristic of patency.

Advantageously the admittance is determined from the ratio of AC values of patient flow and mask pressure, and there is the step of comparing the value of the complex admittance with ranges of values for which the airway is declared patent.

The invention yet further discloses a method for determining the degree of patency of the airway of a patient, the method comprising the steps of:
applying an oscillatory pressure waveform of known frequency, magnitude and phase at an entrance to the patient's airway;
measuring respiratory air flow from the patient;
determining the magnitude and phase of the component of said air flow at said known frequency induced by said oscillatory pressure waveform; and
determining the degree of patency as the location of the complex admittance within the region indicative of patency.

To minimize the effect of the delivery system not supplying a predetermined waveform in the aforementioned method, the pressure waveform actually produced is measured. In this technique we initially apply a waveform of some amplitude at the flow generator, calculate or observe the magnitude of the pressure waveform at the mask, then adjust (typically increasing) the amplitude at the flow generator in order to produce a desired amplitude at the mask. Given that the system is approximately linear for these small signals, the calculation as to how much to increase the driving waveform is a calculation of the radio of the desired to the actual pressure magnitude at the mask. The advantage of this approach is an improvement in the signal to noise ratio.

The invention yet further discloses a method for controlling the administration of CPAP treatment to the airway of a patient by means controllable to supply breathable air to the patient's airway continually at a selectable pressure elevated above atmospheric pressure, the method comprising the step of:
commencing or increasing CPAP treatment pressure if an apnea is occurring, determined by the steps of:
measuring respiratory air flow from the patient as a function of time; and
determining the deviation of said admittance from the centroid of the region of patency.

The invention yet further discloses apparatus for determining patency of the airway of a patient, the apparatus comprising:
means for applying an oscillatory pressure waveform of known frequency to the patient's airway;
means for measuring respiratory air flow from the patient; and
means for determining that the airway is patent if there is an admittance within a patency region at said known frequency induced by said oscillatory pressure waveform.

The invention yet further discloses apparatus for determining the degree of patency of the airway of a patient, the apparatus comprising:
means for applying an oscillatory pressure waveform of known frequency and magnitude to the patient's airway;
means for determining the complex admittance of respiratory air flow from the patient; and means for determining the degree of patency as the deviation of said induced admittance from the centroid of a patency region.

The invention yet further discloses a method of distinguishing between open and closed airway apneas of a patient comprising the steps of:
(i) connecting a respiratory device to a patient via an air delivery tube and a patient interface;
(ii) delivering an alternating pressure waveform to the patient from the respiratory device to the patient via the air delivery tube;
(iii) measuring a flow rate and pressure of air at the respiratory device;
(iv) determining a capacitive component of an air delivery tube impedance;
(v) determining a patient admittance from said measured flow and pressure of air and said capacitive component;
(vi) distinguishing between an open and closed airway apnea on the basis of said patient admittance.

The invention yet further discloses method of distinguishing between open and closed airway apneas of a patient comprising the steps of:
(i) connecting a respiratory device to a patient via an air delivery tube and a patient interface;
(ii) delivering an alternating pressure waveform to the patient from the respiratory device to the patient via the air delivery tube;
(iii) measuring a flow rate and pressure of air at the respiratory device;
(iv) determining an inductive component of an air delivery tube impedance;
(v) determining a patient admittance from said measured flow and pressure of air and said capacitive component;
(vi) distinguishing between an open and closed airway apnea on the basis of said patient admittance.

In another form of the invention patency of the airway is determined to be unknown, or in a "don't know" region. Another aspect of the invention is that patency is defined as having a gradual scale from open to closed. Another aspect is that apnea discrimination regions are defined in the complex plane, the regions not necessarily being contiguous. A further refinement is that the discrimination regions may be functions of the average leak level; in particular, the don't-know regions probably increase in size with increasing leak.

Further forms of the invention are as set out in the claims.

BRIEF DESCRIPTION OF THE DRAWINGS

Embodiments of the invention will now be described with reference to the accompanying drawings, in which.

DETAILED DESCRIPTION

A System Implementing the Invention

Figure 1:
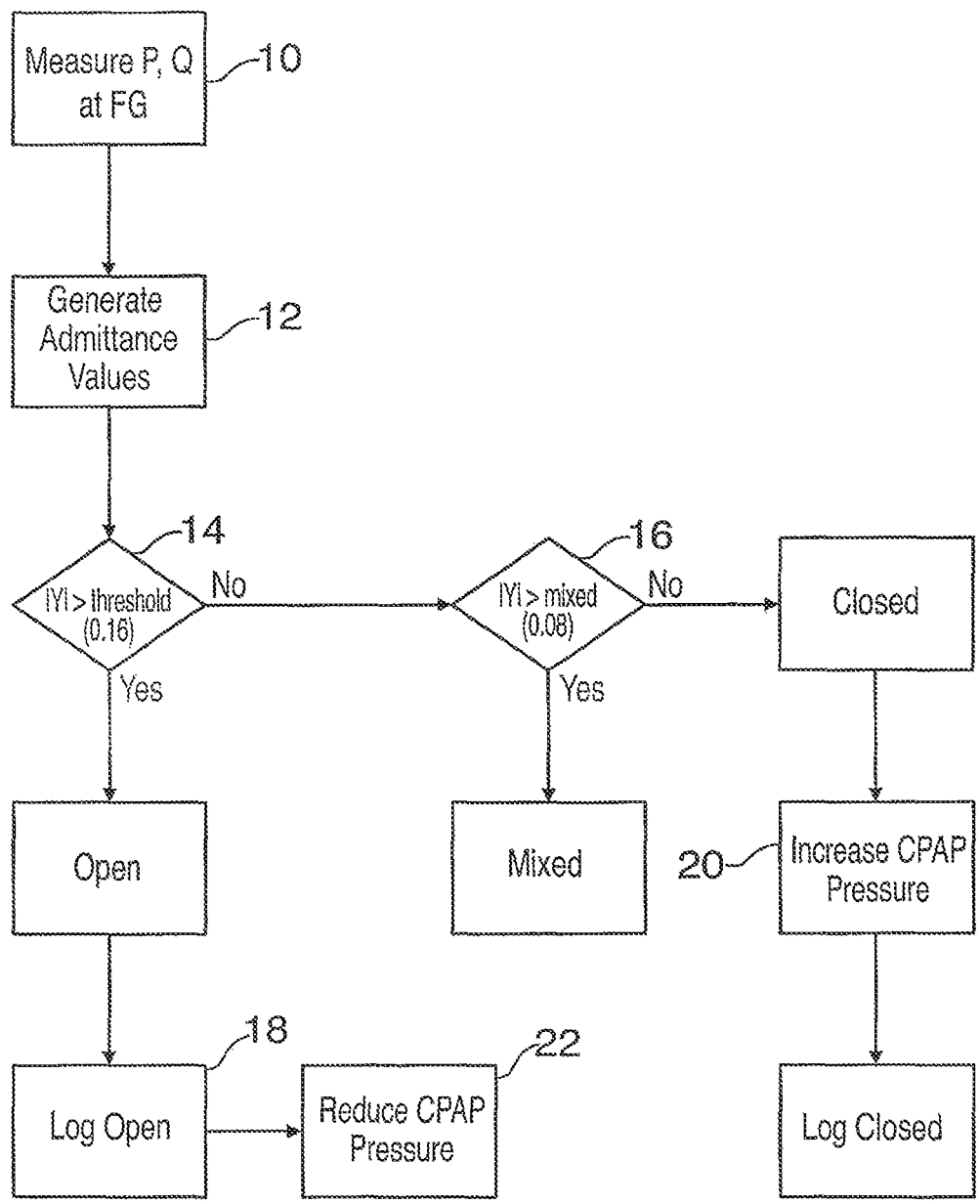
FIG. 1 shows a flow diagram of the basic methodology of an embodiment.

The present invention is an improvement upon the embodiments disclosed in U.S. Pat. No. 5,704,345, which is incorporated by reference in its entirety. FIG. 1 is a flow diagram of the basic methodology of one embodiment of the present invention. The first step 10 of the present invention is the measurement of respiratory flow and pressure at points near the flow generator over time where an apnea is occurring. This information is processed in step 12 to generate admittance values to be used as qualitative measures for subsequent processing. Steps 14-16 detect whether a closed, open or mixed apnea is occurring by comparison of the complex admittance value in a time window with a patency region.

If an apnea is in progress there then follows a determination whether the apnea is open or closed. If an apnea with an open airway is occurring, and, if desired, the event is logged in step 18. If the result of step 16 is that an apnea with a closed airway is occurring, an increase in CPAP treatment pressure occurs in step 20. If desired, step 20 may include the optional logging of the detected abnormality.

In the instance of an apnea with an open airway the CPAP treatment pressure is reduced, in accordance with usual methodologies that seek to set the minimal pressure required to obviate, or at least reduce, the occurrence of apneas. The amount of reduction in step 22 may, if desired, be zero.

The methodology represented in FIG. 1 is of a clinical embodiment, where patient CPAP pressure is controlled over time as appropriate. A purely diagnostic embodiment operates in the same manner except it omits the CPAP pressure increase and pressure decrease actions of step 20 and step 22 respectively.

Figure 2:
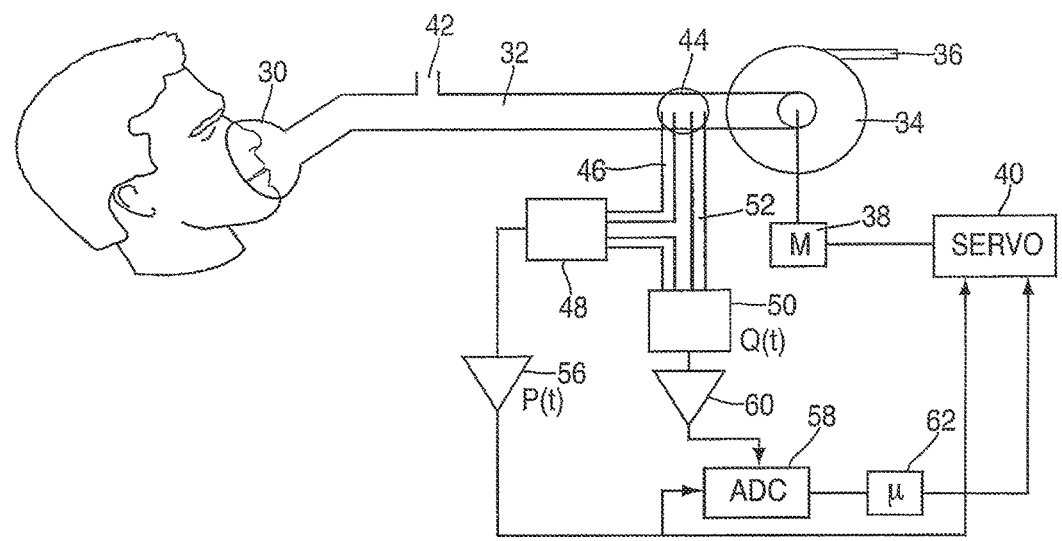
FIG. 2 shows, in diagrammatic form, apparatus embodying the invention.

FIG. 2 shows, in diagrammatic form, clinical CPAP apparatus in accordance with one embodiment for implementing the methodology of FIG. 1. A mask 30, whether either a nose mask and/or a face mask, is sealingly fitted to a patient's face. Fresh air, or oxygen enriched air, enters the mask 30 by flexible tubing 32 which, in turn, is connected with a motor driven turbine (flow generator) 34 to which there is provided an air inlet 36. The motor 38 for the turbine is controlled by a motor-servo unit 40 to either increase or decrease the pressure of air supplied to the mask 30 as CPAP treatment. The mask 30 also includes an exhaust port 42 that is close to the junction of the tubing 34 with the mask 30.

Adjacent to the flow generator 34 is a flow-resistive element 44. This can take the form of an iris across which a differential pressure exists. The mask side of the flow-resistive element 44 is connected by a small bore tube 46 to a pressure transducer 48 and to an input of a differential pressure transducer 60. Pressure at the other side of the flow-resistive element 44 is conveyed to the other input of the differential pressure transducer 50 by another small bore tube 52.

The pressure transducer 48 generates an electrical signal in proportion to the flow pressure, which is amplified by amplifier 56 and passed both to a multiplexer/ADC unit 58 and to the motor-servo unit 40. The function of the signal provided to the motor-servo unit 40 is as a form of feedback to ensure that the static pressure is controlled to be closely approximate to the set point pressure.

The differential pressure sensed across the flow-resistive element 44 is output as an electrical signal from the differential pressure transducer 50, and amplified by another amplifier 60. The output signal from the amplifier 56 therefore represents a measure of the mask or respiratory airflow rate. The controller 62 is programmed to perform a number of processing functions.

The pressure and flow may be considered to be composed of steady state values and AC values, the latter reflecting the effect of a imposed oscillatory signal on the pressure having a frequency of 4 Hz. In what follows, a "steady-state" quantity is either (a) one from which the oscillatory component has been deliberately removed, for example by a filtering operation, or (b) is the result of a calculation based partly or wholly on quantities from which the oscillatory component has been removed, or (c) is a quantity which is calculated based on instantaneous quantities, such as pressure and flow measured at the flow generator (which thus include an oscillatory component), and a model of the airpath and patient leak which either partly or wholly ignores the reactive components of the system and treats it simply as a (possibly nonlinear) system of resistances. The steady state pressure loss along tubing 32 is calculated from the flow through the tube, and knowledge of the static pressure-flow characteristic of the tubing, for example by table lookup. The steady state pressure at the mask is then calculated by subtracting the tube pressure loss. The pressure loss along tube 32 is then added to the desired set pressure at the mask to yield the desired instantaneous pressure at the pressure generator 34. The flow through the exhaust 42 is calculated from the pressure at the mask from the pressure-flow characteristic of the exhaust, for example by table lookup. The steady state mask flow is calculated by subtracting the flow through the exhaust 42 from the flow through the tubing 32. The steady state patient flow is then calculated by subtracting the steady-state estimated leak, which may be determined for example in a CPAP device by a 1st order low pass filter with a time constant of 10 seconds whose input is the instantaneous mask flow, from the steady-state mask flow.

The methodology put into place by the controller 62 will now be described with reference to the apparatus of FIG. 2. If the patient respiratory flow is very low or zero (note that the mask flow will not cease when the patient is apnoeic if there is any leak), a determination of airway patency (steps 14-16) is made by using an externally induced oscillation technique. If the airway is open, but the respiratory muscles are relaxed (i.e. a central apnea with open airway), then small externally originating fluctuations in the mask pressure will induce a small respiratory airflow by inflating and deflating the lungs, and by compressing and decompressing the gas in the lungs. Conversely, if the airway is closed, no airflow will be induced. This is quantified as follows:

Discriminating Apneas by Admittance Thresholds

The admittance Y is given by $$Y = G + iB$$

where G is conductance and B is susceptance

In order to decide whether the airway is open, the complex value of the patient admittance, Y, is compared with a region of values. The value of this threshold may be selected on the basis of the following observations.

An explanation for the angle being a better classifier than the magnitude is possibly related to the interaction of the complex impedances in the circuit. The leak and vent flow are essentially non-linear resistances with no complex (j) component. The patient is basically a resistance and compliance (capacitance) in series to ground. The hose drop also has a complex component in the form of the inertance of the flow. So the magnitude of the overall impedance is influenced by all components (hose, leak, vent flow, patient airway) as they all have real parts. However the imaginary component is the interaction between the inertial hose drop and the capacitive lungs. It is comparing the relative "strengths" of the inertial and capacitive reactances.

It is also possible to use the real and imaginary parts of the impedance rather than the angle and magnitude. This has an advantage of reduced CPU load. The magnitude calculation requires a square root and the angle calculation involves an inverse tan. (Both of these can be done to easily the required accuracy by techniques involving lookup tables, which are computationally fairly cheap.) Using both the real and imaginary or magnitude and angle gives a more robust classification. The grouping of the open and closed values becomes much more apparent.

Figure 4:
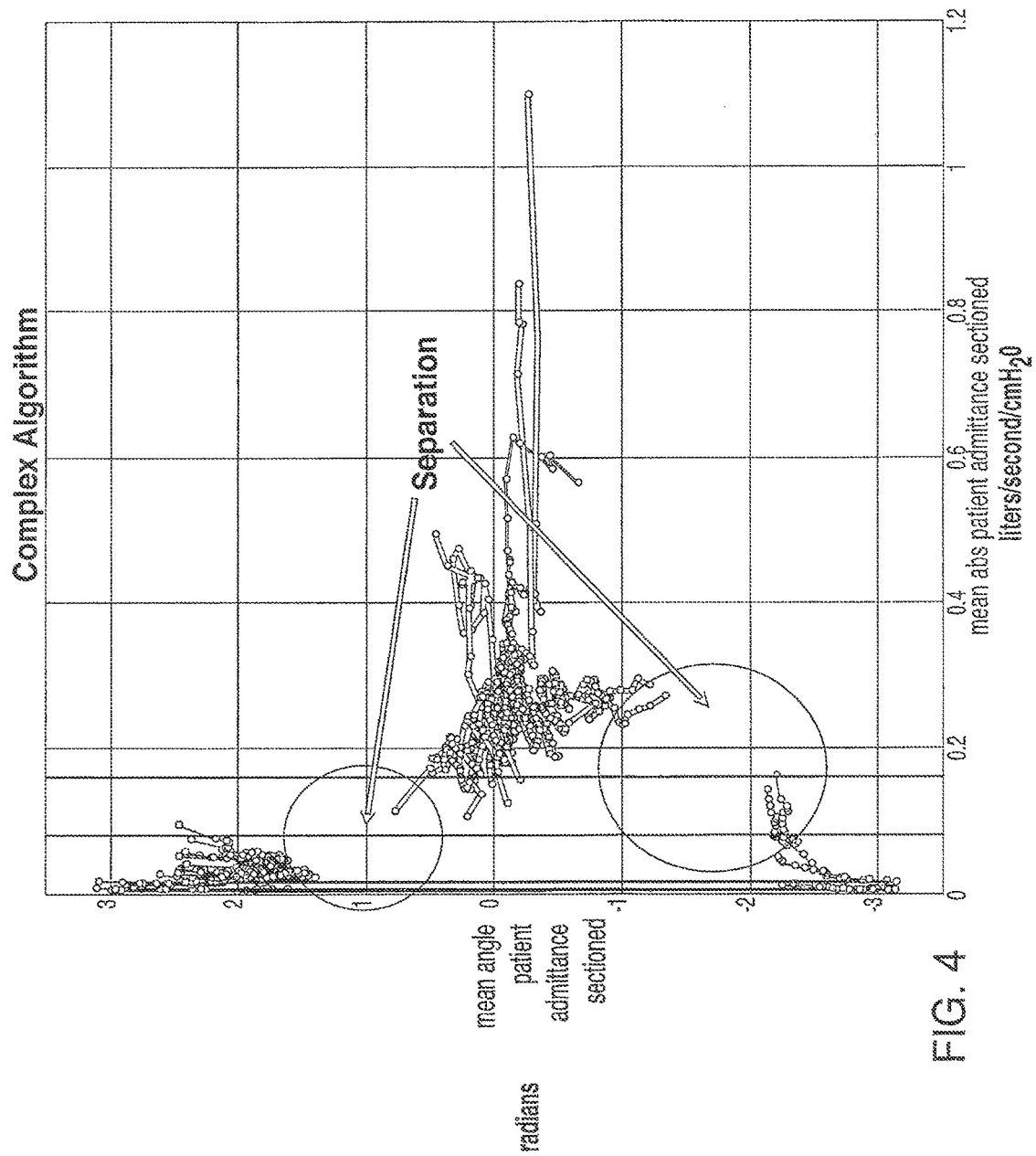
FIG. 4 shows values of the complex admittance based on a detailed algorithm.

As determined from the values in FIG. 4, a possible set of thresholds would be

```
angle = ARG(patient_admittance)
if ( angle < −2 OR angle > 1.2 )
    AirwayState = CLOSED;
else if ( angle < 0.9 AND angle > −1.5 )
    AirwayState = OPEN;
else
    AirwayState = UNKNOWN;
end if
``` where angle is in radians. The acceptable values for the thresholds may be any that permits the separation of values representing open and closed apneas determined from FIG. 4.

The patient resistance at 4 Hz also indicates the state of the airway. This resistance is not the reciprocal of the conductance in the above equation. The patient impedance at 4 Hz is $$Z = R + iX$$

where $$Y = \frac{1}{Z}.$$

The patient resistance R is given by $$R = Re(Z) = Re\left(\frac{1}{Y}\right)$$

In an alternative embodiment R may be used to characterize the state of the airway rather than |Y|.

Calculating Admittance

Patient admittance is calculated by the equation $$Y_{pat} = \frac{Q_{pat,AC}}{P_{mask,AC}},$$

where the numerator is the magnitude of the AC patient flow, which is in effect a measure of the differential (with respect to time) of patient flow. The denominator is the same differential of the mask pressure.

Correcting for Vent Flow and Leak

The patient airflow is determined by subtracting flow through the vent and leakage flow from the inflow to the mask.

$$Q_{pat,AC} = Q_{maskin,AC} - Q_{vent,AC} - Q_{leak,AC}$$

The mean vent flow is determined either from mean mask pressure during the period of measurement, or more preferably from the square of the mean of the square root of the mask pressure during this time (which is also used to make leak calculations). The mask pressure itself is calculated in the conventional way, ignoring AC behavior of the airpath.

AC vent flow is calculated using a linear approximation about the operating point:

$$Q_{vent,AC} = P_{mask,AC} \frac{dQ_{vent}}{dP_{mask}}$$

Modeling Mask Pressure to Determine AC Flow at Mask

The mask pressure is determined by evaluating the coefficients k.sub.1 and k.sub.2 in the equation which gives the pressure drop across the vent as a function of vent flow:

$$P_{mask} = k_1 Q_{vent} + k_2 Q_{vent}^2.$$

Thus to calculate the vent flow at a particular mask pressure, one solves the quadratic equation for vent flow at that mask pressure.

$$\frac{dQ_{vent}}{dP_{mask}}$$

can be obtained by differentiation of the previous equation, which gives $$\frac{dP_{mask}}{dQ} = k_1 + 2k_2 Q_{vent}$$

Since $$\frac{\Delta Q}{\Delta P} \approx \frac{dQ}{dP},$$

a small-signal approximation yields $$\Delta Q \approx \Delta P \frac{dQ}{dP},$$

from which it follows as a reasonable approximation that $$Q_{vent,AC} = \frac{P_{mask,AC}}{k_1 + 2k_2 Q_{vent}}.$$

Calculating Leakage Flow

To complete the calculation of the patient airflow it is necessary to also calculate the leakage flow from the inflow to the mask. The actual leak is calculated over the time period during which the patient 4 Hz admittance is calculated. Typical leak coefficient estimates relate to what happened some time ago, and one may, as in the prior art AutoSet CS and AutoVPAP devices estimate the leak coefficient $K_{leak}$ from $$K_{leak} = \frac{\overline{Q_{nonvent}}}{\sqrt{P_{mask}}}$$

where the overbars indicate the mean over the measurement period. During apnea the leak is equal to the total non-vent flow $$Q_{nonvent} = Q_{FGTotal} - Q_{vent}$$

and during breathing, the leak is (to a good approximation) equal to the average non-vent flow. In the above estimation of $K_{leak}$, all quantities are calculated without reference to the AC characteristics of the airpath, based on instantaneous values, treating the airpath as a nonlinear resistor.

The model for instantaneous leak, both DC (on which the above formula for $K_{leak}$ is based) and AC is $$Q_{leak} = K_{leak} \sqrt{P_{mask}}$$

and, as with vent flow, the AC component (at 4 Hz) of leak flow is found using the small-signal approximation $$Q_{leak,AC} = P_{mask,AC} \frac{dQ_{leak}}{dP_{mask}}$$

where we may calculate $$\frac{dQ_{leak}}{dP_{mask}}$$

by differentiating the above equation directly, giving $$\frac{dQ_{leak}}{dP_{mask}} = \frac{K_{leak}}{2\sqrt{P_{mask}}}.$$

The mean for $\sqrt{R_{mask}}$, may be either $\sqrt{\overline{P_{mask}}}$ or $\overline{\sqrt{P_{mask}}}$. The latter is preferred (because it gives an unbiased estimate of the mean value of $$\frac{dQ_{leak}}{dP_{mask}}$$

when $P_{mask}$ is not constant, and we have already calculated it in order to estimate $K_{leak}$), yielding $$\frac{dQ_{leak}}{dP_{mask}} = \frac{\overline{Q_{nonvent}}}{2(\overline{\sqrt{P_{mask}}})^2}.$$

Determination of AC Values

Throughout this description, the AC values referred to are determined from measurements as trigonometric Fourier components at the exciting frequency. This is an improvement over the prior art use of the forced oscillation technique, which used square waves as an orthonormal set of functions.

All AC quantities are calculated as complex numbers. In particular, the AC pressure and flow at the mask are calculated by finding the sine and cosine components of instantaneous pressure and flow oven the period of measurement using the inner products with the sine and cosine function respectively, yielding component coefficients $c_s$ and $c_c$, then writing either $c_s + ic_c$ or $c_c + ic_s$ as the AC value. (Either of these two forms is used, the two forms differing merely in a phase shift, but the one form is used consistently throughout). Alternatively other standard methods of estimating the amplitude and phase of the sinusoidal component of the pressure and flow at the exciting frequency may be used, such as least-squares fitting of a sine and a cosine.

Explicitly we have $$c_c = \frac{1}{T}\int_0^{2\pi/w} f(t)\sin(\omega t)\,dt;$$

$$c_C = \frac{1}{T}\int_0^{2\pi/w} f(t)\cos(\omega t)\,dt;$$

where the exciting frequency is T/2B, T is a normalizing factor, and the integral may be replaced by a summation using discrete sampled values of sine and cosine. f(t) is any function whose Fourier coefficients are required.

All quantities are determined over a 6 second sliding window (the "admittance window") symbolically indicated as t=0. An admittance calculation can in principle be made at the algorithmic sampling frequency (say 50 Hz), but for clinical purposes this is not essential, and the calculation may be efficiently performed at the end of every 4 Hz cycle. Alternatively, calculation of admittance at 2 Hz or even 1 Hz frequencies is reasonable for clinical purposes.

Due to motor controller delays, the first cycle (250 ms) of the pressure waveform may not be sinusoidal, and there will be some delay in setting up a steady state in the airpath, so the first 250 ms of data may be ignored.

The sine and cosine values would be stored in a table generated at startup or specified as constants in the source code. Sufficient accuracy is provided if multiplications are fixed point, 16 bit*16 bit with a 32 bit result, assuming of course that overflow of the sum does not occur, and there are no numerical stability issues with this approach. Thus the computational cost is relatively small.

Modeling Impedance on a Two Port Network

The calculation of AC pressure at the mask and AC flow entering the mask is in one embodiment determined from a 2-port electrical network analogue of the flow in the system at a particular frequency.

Figure 3:
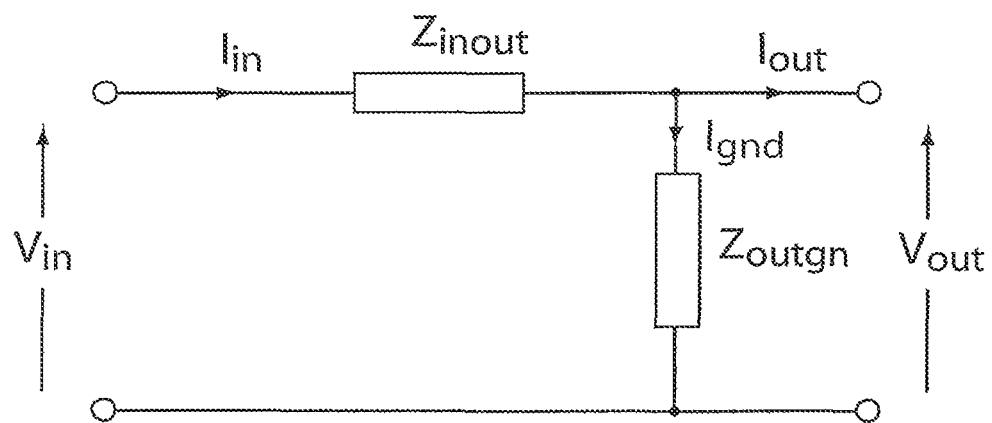
FIG. 3 shows an electronic analogue of the 2-port analysis of the present invention.

From FIG. 3, routine circuit analysis gives $$V_{out} = V_{in} - I_{in}Z_{inout}$$

$$I_{out} = I_{in} - \frac{V_{out}}{Z_{outgnd}}$$

and of course these correspond to pressure and the mask and flow entering the mask respectively. Explicitly:

$$P_{mask,AC} = P_{FG,AC} - Q_{FG,AC}F_{inout}$$

$$Q_{maskin,AC} = Q_{FG,AC} - \frac{P_{mask,AC}}{Z_{outgnd}}$$

The impedances $Z_{inout}$ and $Z_{outgnd}$ are taken to be functions of average flow. These impedances are measured for a particular airpath at a number of average flow levels (see below for details). The average total flow generator flow during the admittance window is determined, and for each of $Z_{inout}$ and $Z_{outgnd}$, is used to linearly interpolate between the measured impedances to determine the impedance at that average flow level.

The inlet and outlet AC flows and AC pressures are determined over a period of 30 seconds (to reduce noise) using the standard inner product method described above for the calculation of Fourier coefficients, yielding complex values. These values are used to calculate the 2-port parameters (refer to FIG. 1, where voltages and currents in that figure correspond to pressures and flows respectively in the following), by:

$$Z_{inout} = \frac{P_{in} - P_{out}}{Q_{in}}$$

$$Z_{outgnd} = \frac{P_{out}}{Q_{in} - Q_{out}}$$

If the denominators are very small or zero, the impedances are taken to have some numerically very large value in relation to typical airpath impedances.

The Hose Pressure Drop Theoretical Model

The hose drop is the pressure difference between the internal mask pressure and the FG pressure. It is the pressure loss across all components that are placed before the mask. This includes mufflers, humidifiers, AB filters and the mask connection hose.

The complete hose drop is made up of the resistive hose drop as well as the inertial pressure drop $$P_{hosedrop} = K_1 Q_{FG}^2 + K_2 Q_{FG} + K_L \frac{dQ_{FG}}{dt}$$

$K_1, K_2$=empirically derived constants
$K_L$=theoretically determined flow inertance constant
$Q_{FG}$=FG Flow $$K_L = \frac{\rho l}{A},$$

$\rho$=air density (1.19 kg/m$^3$)
l=tube length (2 or 3 m)
A=cross section area 4

$$\left(\frac{\pi d^2}{4}, d = 0.019 \text{ m}\right)$$

In the case of masks such as the ResMed Activa and Swift masks there is another tube between the main hose and the mask. This must also be taken into account in the inertial constant.

The mean hose drop is made up of purely the resistive part (the over bar indicates mean):

$$\overline{P_{hosedrop}} = K_1 \overline{Q}_{FG} + K_2 \overline{Q}_{FG}$$

$K_1, K_2$=empirically derived constants $\overline{Q}_{FG}$=Mean FG Flow

In order to calculate the AC hose drop some linearization is necessary. The resistive and inertial components are separated. The resistive component is derived by linearizing the above mean hose drop formula about the operating point.

$$\frac{dP_{hosedrop}}{dQ_{FG}} = 2K_1 Q_{FG} + K_2$$

$$P_{hosedrop\ resistive,AC} = (2K_1 \overline{Q}_{FG} + K_2)Q_{FG,AC}$$

The AC hose drop is thus the AC flow multiplied by gradient of the hose non-linear resistance at the location around which the small oscillation occurs. For the derivation it is assumed that the oscillations are of a small magnitude compared to the change in the gradient of the hose resistance.

The inertial component is a constant multiplied by the time derivative of the FG flow. By standard linear circuit theory, an inductance L has impedance sL, which for sinusoidal signals at the frequency $\omega$ is $j\omega L$. The inertial hose drop component then becomes:

$$P_{hosedrop\ iner\ tan\ ce,AC} = K_L j\omega Q_{FG,AC}$$

$$\omega = 2\pi f$$

Combining the two gives $$P_{drop,AC} = (2K_1\overline{Q}_{FG} + K_2 + K_L j\omega)Q_{FG,AC}$$

Mask Pressure

The mask pressure is the FG pressure minus the hose pressure drop:

$$P_{mask} = P_{FG} - P_{hose\ drop}$$

$$P_{mask,AC} = P_{FG,AC} - P_{hose\ drop,AC}$$

EXAMPLES

In FIG. 4 a plot is presented in which the thick lines represent open apneas and the thin lines represent closed apneas. The horizontal axis represents the absolute magnitude of the admittance, while the vertical axis represents the phase of the complex admittance. As may be seen from the figure, there is a complete separation of the open apneas, represented by the thick curves in the center of the graph, from the closed apneas, represented by the two thinner curve regions, one near the origin and the other at the extreme upper value of the y axis. If one looks only at the absolute value of the admittance, in effect by projecting all of the data onto the x axis, the separation of the data is lost, with the projection of the thin (closed apnea) curves meeting the projection of the thick (open apnea) data.

FIG. 4 shows the result of plotting patient admittance data calculated according to the formulas above. The x axis values are the average absolute value of the patient admittance. The y axis values are the phase angle of the patient admittance. As may be seen from FIG. 4 there is a clean separation of the values for closed apneas and for open apneas.

Figure 5:
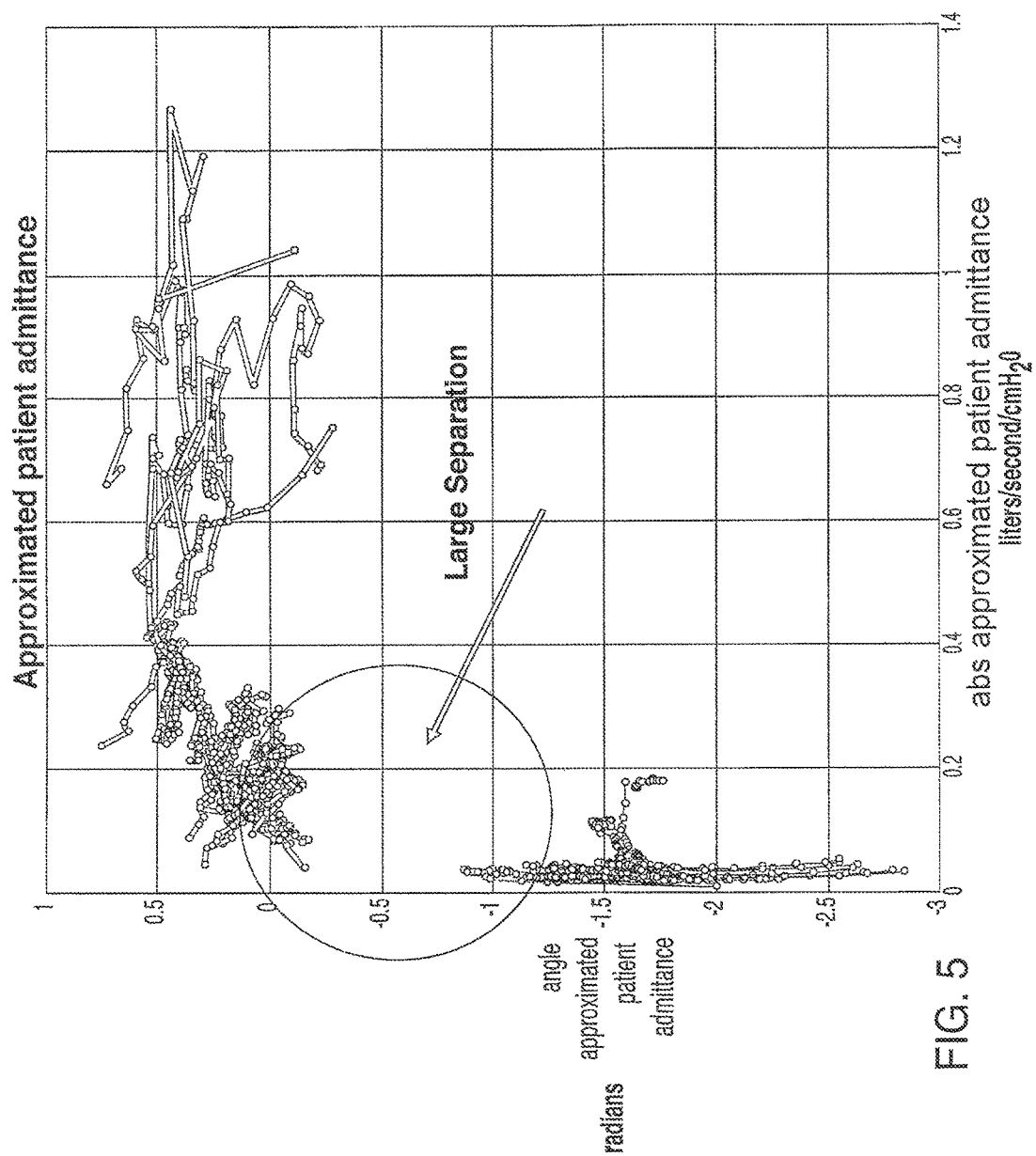
FIG. 5 shows values of the complex admittance based on a simplified algorithm.

FIG. 5 shows the result of plotting patient admittance where instead of the previous calculation of admittance a value for the complex admittance is determined from a model that is essentially independent of the modelling details of any particular configuration of mask or ventilation circuit. In particular, the data for FIG. 5 were determined by using a simple leak orifice model $P=(KQ)^2$. It may be seen from FIG. 5 that the open and closed apneas result in separated regions of the plot of the complex admittance.

Moderate (Approximated Patient Admittance) Algorithm

The third algorithm attempts to approximate the patient admittance by generically modeling the patient circuit and combining the leak and vent flows.

The patient circuit is modeled in the same way as the Complex algorithm above, however the constants are fixed at those for a 2 m hose with AB filter.

The leak and vent flow modeling are combined into one parameter which is the non patient flow. This is modeled as Leak+Vent Flow The leak and vent flow are combined and modeled as using the following equations:

The leak orifice can be approximated at runtime using:

$$K_{leak} = \frac{\overline{Q_{FG}}}{\sqrt{\overline{P_{mask}}}}$$

The instantaneous leak is then calculated using $$Q_{leak} = K_{leak}\sqrt{P_{mask}}$$

Using small signal approximation we can say that $$Q_{leak,AC} = P_{mask,AC}\frac{dQ_{leak}}{dP_{mask}}$$

where $$\frac{dQ_{leak}}{dP_{mask}} = \frac{K_{leak}}{2\sqrt{P_{mask}}}$$

(from instantaneous leak equation) substituting in $K_{leak}$ we get $$Q_{leak,AC} = P_{mask,AC}\frac{\overline{Q_{FG}}}{2(\sqrt{\overline{P_{mask}}})^2},$$

as we are dealing with small mean Pmask changes we can approximate $$(\sqrt{\overline{P_{mask}}})^2 \text{ with } \overline{P_{mask}}$$

so the AC leak becomes $$Q_{leak,AC} = P_{mask,AC}\frac{\overline{Q_{FG}}}{2\sqrt{\overline{P_{mask}}}},$$

Approximated Patient Flow

The patient flow is then $$Q_{patient,AC} = Q_{FG,AC} - Q_{leak,AC}$$

Qleak is the leak flow combined with the vent flow (all non patient flow).

Classification

There are a number of ways to use the approximated admittance to classify the airway state. Good separation in just the angle can be seen when plotting the angle vs magnitude of the admittance. Therefore a simple classification would be to have two thresholds, but purely on angle. However the calculation of the angle involves a division and an inverse tan, requiring more calculation. It is suggested that it is preferable to have the real and imaginary parts of the admittance used instead.

Thresholds

The simplest thresholds which provide good classification accuracy are simple straight diagonal lines. These are of the form y>x+b and y<x+c. In this case when plotting the imaginary part (y) vs the real part (x) of the admittance, CLOSED is y>x+b, and OPEN is y<x+c. Based on the floating-point algorithm the values for the constants were b=0, c=−0.03. This gave no misclassification. Any other curves that separate the data regions could be used, but the linear separation reduces the complication of the threshold calculations and is for that reason preferred.

Alternative Embodiment

In an alternative embodiment, the patient impedance is first measured during normal breathing, for example at the end of the expiratory portion of the breath. This measured impedance is averaged over a predetermined time period. The average normal impedance value is compared to the measured impedance during a detected apnea. The determination of an open or closed airway based on impedance is then performed.

This alternative method has the advantages of taking into account the entire patient circuit including the patient's airway and makes unnecessary the requirement for the patient circuit components to be characterized. In addition this system automatically takes into account the current altitude and ambient conditions.

The system allows for plausibility data to be generated using fuzzy logic. For example if a strange impedance measurement is obtained when the patient is breathing normally then the algorithm can detect this and deliver an implausible result. Also wildly varying impedance values may indicate a fault in the system. The system may also detect if inappropriate components are present in the system and deliver an error.

The invention claimed is:

1. An apparatus for providing a supply of continuous positive airway pressure to an airway of a patient at a desired treatment pressure, the apparatus comprising:
  a flow generator adapted to provide a supply of continuous positive airway pressure, the flow generator adapted to couple with an air delivery tube coupled with a patient interface configured to sealingly engaged with a face of the patient;
  a means for determining respiratory air flow and pressure in the patient interface;
  a means for measuring a patient impedance of the airway during a period of a breathing cycle when an apnea is not occurring; and
  a controller to control operation of the flow generator based on the determined respiratory air flow and pressure,
  the controller configured in use to detect the occurrence of an apnea and to determine patency of the airway of the patient during the apnea by performing:
    controlling application of an oscillatory pressure waveform of known frequency to the patient interface for delivery to the airway of the patient in use;
    measuring an apnea impedance of the airway during the apnea; and
    comparing the measured apnea impedance with the patient impedance to determine whether the airway is patent.

2. The apparatus according to claim 1, wherein the means for determining respiratory air flow and pressure includes measuring the air flow and pressure using at least one sensor.

3. The apparatus according to claim 2, wherein the at least one sensor is a differential pressure sensor.

4. The apparatus according to claim 2, wherein the patient impedance is determined by the controller controlling application of an oscillatory pressure waveform of known frequency to the patient interface for delivery to the patient's airway during the period of the breathing cycle when an apnea is not occurring.

5. The apparatus according to claim 1, wherein the period of the breathing cycle is at an end of an expiratory portion of a breath.

6. The apparatus according to claim 1, wherein the patient impedance is a determined average of measured patient impedance over a predetermined time period.

7. The apparatus according to claim 1, wherein the controller is configured to perform a plausibility check on the measured patient impedance.

8. The apparatus according to claim 7, wherein if the measured patient impedance value is determined to be implausible, the controller indicates that a fault has occurred.

9. The apparatus according to claim 1, wherein the known frequency is between 1 and 16 Hz.

10. The apparatus according to claim 9, wherein the known frequency is between 2 and 8 Hz.

11. The apparatus according to claim 9, wherein the known frequency is 4 Hz.

12. The apparatus according to claim 1, wherein the controller is further configured to increase the treatment pressure in response to the determination of a patent airway.

13. The apparatus according to claim 1, wherein the controller is further configured to reduce the treatment pressure in response to the determination of a closed airway.

14. A method for operating a respiratory device with a flow generator to determine patency of an airway of a patient, the method comprising:
  controlling generation of a first oscillatory pressure waveform of known frequency to a patient interface during a period of a breathing cycle when an apnea is not occurring;
  measuring respiratory air flow and pressure at the flow generator;
  determining a patient impedance of the airway;
  determining that an apnea is occurring based on the measured respiratory air flow;
  controlling generation of a second oscillatory pressure waveform of known frequency to the patient interface during the apnea;
  determining an apnea impedance of the airway during the apnea; and
  determining that the airway is patent by comparing the apnea impedance with the patient impedance.

15. The method according to claim 14, wherein the period of the breathing cycle is at an end of an expiratory portion of the breath.

16. The method according to claim 14, wherein the patient impedance is determined as an average of measured patient impedance over a predetermined time period.

17. The method according to claim 14, further including controlling with the respiratory device a continuous positive air pressure in the patient interface at a desired treatment pressure.

18. The method according to claim 17, wherein if the apnea is classified as an open apnea determining a reduction of the treatment pressure.

19. The method according to claim 17, wherein if the apnea is classified as a closed apnea determining an increase of the treatment pressure.

* * * * *